US012808871B2

(12) United States Patent
Yasui et al.

(10) Patent No.: US 12,808,871 B2

(45) Date of Patent: Nov. 24, 2026

(54) METHOD FOR TESTING BRAIN TUMORS

(71) Applicant: CRAIF INC., Tokyo (JP)

(72) Inventors: Takao Yasui, Nagoya (JP); Yoshinobu Baba, Nagoya (JP); Atsushi Natsume, Nagoya (JP)

(73) Assignee: CRAIF INC., Tokyo (JP)

( * ) Notice: Subject to any disclaimer, the term of this patent is extended or adjusted under 35 U.S.C. 154(b) by 1209 days.

(21) Appl. No.: 17/763,786

(22) PCT Filed: Sep. 24, 2020

(86) PCT No.: PCT/JP2020/035899

§ 371 (c)(1),
(2) Date: Mar. 25, 2022

(87) PCT Pub. No.: WO2021/060311

PCT Pub. Date: Apr. 1, 2021

(65) Prior Publication Data

US 2022/0349888 A1 Nov. 3, 2022

(30) Foreign Application Priority Data

Sep. 27, 2019 (JP) ................................ 2019-177615

(51) Int. Cl.

| | |
|---|---|
| ***C12Q 1/68*** | (2018.01) |
| ***C12P 19/34*** | (2006.01) |
| ***C12Q 1/6809*** | (2018.01) |
| ***C12Q 1/6886*** | (2018.01) |
| ***G01N 33/575*** | (2026.01) |

(52) U.S. Cl.

CPC ......... *G01N 33/575* (2026.01); *C12Q 1/6809* (2013.01); *C12Q 1/6886* (2013.01); *C12Q 2600/158* (2013.01); *C12Q 2600/178* (2013.01)

(58) Field of Classification Search

None

See application file for complete search history.

(56) References Cited

U.S. PATENT DOCUMENTS

| | | | |
|---|---|---|---|
| 2011/0301221 A1 | 12/2011 | Lin et al. | |
| 2013/0330727 A1 | 12/2013 | Audrey | |
| 2015/0368724 A1 | 12/2015 | Aharonov et al. | |
| 2018/0258483 A1* | 9/2018 | Van Keuren-Jensen | C12Q 1/6883 |
| 2020/0255906 A1* | 8/2020 | Yasui | C12Q 1/6886 |

FOREIGN PATENT DOCUMENTS

| | | | |
|---|---|---|---|
| EP | 3438266 | A1 | 2/2019 |
| WO | 2010/042831 | A2 | 4/2010 |
| WO | 2017/171039 | A1 | 10/2017 |

OTHER PUBLICATIONS

MiScript™ miRNA PCR Array (384-well, 384HC) Human miRBase Profiler HC Plate 6 (2012) Qiagen. Printed from geneglobe.qiagen.com. (Year: 2012).*

3D-Gene Human miRNA V21_1.0.0 ( Dec. 19, 2015), Toray Industries, Inc., Platform GPL21263 printed from https://www.ncbi.nlm.nih.gov (Year: 2015).*

Yasui et al., "Unveiling massive numbers of cancer-related urinary-microRNA candidates via nanowires" Sci. Adv. 2017; 3 : e1701133 Dec. 15, 2017 (Year: 2017).*

Atanu Ghorai, et al. "miRNA gene counts in chromosomes vary widely in a species and biogenesis of miRNA largely depends on transcription or post-transcriptional processing of coding genes" Front. Genet., Apr. 28, 2014, Sec. RNA, vol. 5. (Year: 2014).*

Vivian G. Cheung, et al. "Natural variation in human gene expression assessed in lymphoblastoid cells" Nature Genetics, vol. 33 , Mar. 2003, pp. 422-425. (Year: 2003).*

J. Perren Cobb, et al."Sepsis gene expression profiling: Murine splenic compared with hepatic responses determined by using complementary DNA microarrays" Crit Care Med 2002 vol. 30, No. 12 (Year: 2002).*

Partial Supplementary European Search Report issued on Oct. 20, 2023, in European Patent Application No. 20870120.1 (15 pages).

Sharma, Anju, et al. "Identificatin of Serum MicroRNA Signatures for Diagnosis of Mild Traumatic Brain Injury in a Closed Head Injury Model" PLOS One, vol. 9, Issue 11, e112019, Nov. 2014.

Tumilson, Charlotte A., et al. "Circulating MicroRNA Biomarkers for Glioma and Predicting Response to Therapy" Molecular Neurobiology, vol. 50, No. 2, pp. 545-558, Apr. 2014.

International Search Report received in application No. PCT/JP2020/035899, mailed Dec. 8, 2020, 5 pages, with translation.

Kitano et al., "Search for urinary biomarkers of glioma by machine learning," Programs and abstracts of the 37th Annual Meeting of the Japan Society for Neuro-Oncology, Nov. 15, 2019, p. 217, p.11-1-11, entire text, non-official translation.

Roth et al., "A specific miRNA signature in the peripheral blood of glioblastoma patients" Journal of Neurochemistry, 118, pp. 449-457, 2011.

Kitano, Yotaro, et al., "Machine learning to detect gliomas in urine-based liquid biopsy", 2023, Nagoya, Japan.

* cited by examiner

*Primary Examiner* — Stephen T Kapushoc

(74) *Attorney, Agent, or Firm* — McBee, Moore & Vanik IP, LLC

(57) ABSTRACT

Provided are a novel biomarker for a brain tumor and a method for using the same. A method for detecting a brain tumor, the method comprising the step of detecting specific miRNA as biomarker.

5 Claims, No Drawings

METHOD FOR TESTING BRAIN TUMORS

CROSS-REFERENCE TO RELATED APPLICATIONS

This application is the National Stage entry of International Application No. PCT/JP2020/035899, filed 24 Sep. 2020, which claims priority to Japan No. 2019-177615, filed 27 Sep. 2019.

BACKGROUND

Field

TECHNICAL FIELD

The present invention relates to methods and the like for testing a brain tumor.

Description of Related Art

Brain tumor is a collective term for tumors in the skull and is divided into two types: primary and metastatic brain tumors. Brain tumors are usually detected in image inspections of patients who complain of subjective symptoms such as headache, vomiting, paralysis, aphasia/dysarthria, and disturbed consciousness, and minor head injuries, and image inspections in medical examinations such as brain docks. In image inspections, CT, MRI, cerebral angiography, and the like are utilized. If a brain tumor is detected by image inspection, the tumor is removed by craniotomy and the tissue removed is used for pathologic diagnosis. At present, tumor markers for discovering malignant brain tumors with markers in the blood have not become popular in clinical practice.

MicroRNAs are small in vivo molecules composed of 20-25 bases, and are considered promising as biomarkers for predicting disease onsets. In Patent Literature 1, a plurality of miRNA that can be used for biomarkers of malignant brain tumors from blood that can be collected with low invasion have been reported.

PRIOR ART LITERATURE

Patent Literature

Patent Literature 1: WO 2017/171039

SUMMARY

Technical Problem

It is a problem to be solved by the present invention to provide novel biomarkers of brain tumor and methods of utilizing the same.

Solution to Problem

As a result of diligent research in view of the above problem, the present inventors have found that a brain tumor can be inspected using at least one selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p, in a sample derived from body fluid collected from a subject, as biomarker. As a result of further research on the basis of this finding, the present inventors have completed the present invention. That is, the present invention includes the following aspects.

Item 1. A method for testing a brain tumor, comprising:

(1) the step of detecting at least one biomarker selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p, in a sample derived from a body fluid collected from a subject.

Item 2. The testing method according to Item 1, comprising: (2) the step of determining whether the subject has a brain tumor, based on the amount or concentration of the biomarker detected in step (1).

Item 3. The testing method according to Item 1 or 2, wherein said biomarker is at least one selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, and miR-509-5p.

Item 4. The testing method according to any one of Items 1 to 3, wherein said biomarker is at least one selected from the group consisting of: miR-345-3p, miR-208a-5p, miR-188-3p, miR-504-5p, miR-199a-5p, miR-93-3p, miR-328-5p, and miR-483-3p.

Item 5. The testing method according to Item 3 or 4, wherein said biomarker is 3 or more biomarkers.

Item 6. The testing method according to any one of Items 3 to 5, wherein said brain tumor is glioma.

Item 7. The testing method according to Item 1 or 2, wherein said biomarker is at least one selected from the group consisting of: miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p.

Item 8. The testing method according to any one of Items 1, 2 and 7, wherein said biomarker is at least one selected from the group consisting of miR-6070, miR-450a-2-3p, miR-4638-3p, and miR-20a-3p.

Item 9. The testing method according to Item 7 or 8, wherein said biomarker is 3 or more types of biomarkers.

Item 10. The testing method according to any of Items 1 to 9, wherein said body fluid is urine.

Item 11. The testing method according to any of Items 1 to 10, wherein said body fluid sample is an extracellular vesicle of urine.

Item 12. The testing method according to any one of Items 1 to 11, wherein the subject is human.

Item 13. A test agent for brain tumor, comprising a detecting agent of at least one biomarker selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p.

Item 14. A test kit for brain tumor, comprising a detecting agent of at least one biomarker selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p.

Item 15. A method of screening an active ingredient of preventive or therapeutic agent for brain tumor, wherein the amount or concentration of at least one biomarker selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p in a sample derived from a body fluid taken from an animal treated with a test substance is used as indicator.

Item 16. A method of assessing an inducibility or exacerbation of a brain tumor, wherein the amount or concentration of at least one biomarker selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p, in a sample derived from a body fluid taken from an animal treated with a test substance is used as indicator.

DETAILED DESCRIPTION OF A PREFERRED EMBODIMENT

According to the present invention, biomarkers of brain tumor can be provided. Utilizing the biomarkers may enable testing of brain tumors, screening of active ingredients for prevention or therapeutic agent of brain tumors, evaluation of inducibility or exacerbation of brain tumor, and the like.

Description of Embodiments

As used herein, the terms “containing” and “including” include the concepts of “containing”, “including”, “consisting substantially of” and “consisting solely of”.

1. Testing Method of Brain Tumors

The present invention, in one aspect, relates to a method of testing a brain tumor, comprising (1) the step of detecting at least one of the biomarkers selected from the group consisting of: miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p, in a sample derived from body fluid collected from a subject (may be referred to herein as “testing method of the present invention”). This will be described below.

1-1. Step (1)

The types of brain tumor to be examined are not particularly limited. Brain tumors include, for example, glioma, meningioma, primary malignant lymphoma of the central nervous system, pituitary adenoma, schwannoma, craniopharyngioma and the like. Among these, glioma, meningioma and the like are preferably mentioned as objects of the test method of the present invention. Brain tumors of all classes, grades, and stages of brain tumors in the various classification criteria for brain tumors are the targets of the test.

The subject is an object organism of the testing method of the present invention, and the biological species are not particularly limited. The biological species of the subject include, for example, various mammals such as humans, monkeys, mice, rats, dogs, cats, rabbits, and the like, and preferably humans.

The state of the subject is not particularly limited. The subjects include, for example, a sample of which it is not clear whether it has a brain tumor or not, a sample of which it has already been determined by another method that it has a brain tumor, a sample of which it has already been determined by another method that it does not have a brain tumor, a sample which is being treated for a brain tumor, and the like.

Body fluids are not particularly limited. The body fluids include, for example, urine, whole blood, serum, plasma, cerebrospinal fluid, saliva, joint fluid, tissue fluid (including bronchoalveolar lavage fluid), sweat, tears, sputum, nasal mucus, and the like, and preferably urine.

The sample derived from a body fluid may be a body fluid itself or a sample obtained by performing any operation (separation, purification, drug addition, or the like) to a body fluid. Extracellular vesicles of body fluid are preferred as the body fluid-derived sample, and extracellular vesicles of urine are particularly preferred. The body fluid-derived sample may be adopted by 1 type alone or in combination of 2 or more types thereof.

Extracellular vesicles are not particularly limited as long as they are membrane vesicles that are secreted, released, or the like, from cells. Extracellular vesicles are usually defined as membrane vesicles that carry intracellular proteins and genetic information (mRNA, microRNA, and the like) out of the cell and are responsible for communication between cells locally and throughout the body. Extracellular vesicles include, for example, exosomes, microendoplasmic reticulum, apoptotic bodies, ectosomes, microparticles, secretory microvesicles, and the like. Of these, exosomes are preferred.

Extracellular vesicles may be purified, separated, concentrated, and the like, from urine according to or following known methods. Methods of purifying, separating, concentrating, and the like extracellular vesicles include, for example methods using nanowires, ultracentrifugation methods (for example, a pellet down method, sucrose cushion methods, density gradient centrifugation methods, and the like), methods using an immunoaffinity carrier, gel filtration methods, field-flow fractionation methods, FACS methods, and the like. Further, purification, separation, concentration, and the like of extracellular vesicles can be performed using commercially available kits. Among these methods, the methods using nanowires are particularly preferable from the viewpoint of efficiently capturing the urinary extracellular endoplasmic reticulum. Methods utilizing nanowires are described, for example, in WO 2015/137427. These methods may be employed by 1 type alone, or 2 or more types thereof may be employed in combination.

The detection targets of step (1) is at least one type of biomarker (these may be summarized as "target biomarkers" in this Specification) selected from the group consisting of miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, miR-509-5p, miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p.

The target biomarker is a biomarker whose expression level is changed in brain tumor, and the brain tumor can be differentiated by using this biomarker as indicator.

Among the target biomarkers, at least one biomarker (BM1) selected from the group consisting of miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p, miR-301a-5p, miR-140-3p, miR-122-5p, miR-335-3p, miR-539-5p, miR-374b-5p, miR-144-5p, miR-196a-5p, miR-124-3p, miR-363-5p, miR-376b-5p, miR-367-5p, miR-29a-3p, miR-146a-3p, miR-216a-5p, miR-148a-5p, miR-99a-5p, and miR-509-5p can preferably be utilized as biomarker for gliomas.

Among BM1, at least one biomarker (BM1A) selected from the group consisting of miR-122-5p, miR-124-3p, miR-1251-5p, miR-125b-2-3p, miR-140-3p, miR-143-3p, miR-144-5p, miR-146a-3p, miR-148a-5p, miR-181b-2-3p, miR-188-3p, miR-196a-5p, miR-202-5p, miR-204-3p, miR-20b-3p, miR-216a-5p, miR-224-3p, miR-26a-1-3p, miR-27b-3p, miR-296-3p, miR-29a-3p, miR-29b-2-5p, miR-301a-5p, miR-32-3p, miR-335-3p, miR-338-5p, miR-363-5p, miR-367-5p, miR-374b-5p, miR-376b-5p, miR-411-3p, miR-504-5p, miR-539-5p, miR-541-3p, miR-598-5p, miR-93-3p, and miR-99a-5p is a target biomarker whose amount in a brain tumor sample tends to be higher than the amount in a healthy sample.

Among BM1, at least one biomarker (BM1B) selected from the group consisting of miR-199a-5p, miR-208a-5p, miR-30c-2-3p, miR-328-5p, miR-345-3p, miR-483-3p, and miR-509-5p is a target biomarker whose amount in a brain tumor sample tends to be lower than an amount in a healthy sample.

Among BM1, from the viewpoint of larger AUC (Area Under the Curve) at the time of determination, miR-345-3p, miR-208a-5p, miR-188-3p, miR-504-5p, miR-199a-5p, miR-93-3p, miR-328-5p, miR-483-3p, miR-204-3p, miR-411-3p, miR-1251-5p, miR-30c-2-3p, miR-26a-1-3p, miR-27b-3p, miR-338-5p, miR-541-3p, miR-224-3p, miR-143-3p, miR-32-3p, miR-202-5p, miR-296-3p, miR-598-5p, miR-125b-2-3p, miR-20b-3p, miR-181b-2-3p, miR-29b-2-5p and the like are preferable, and miR-345-3p, miR-208a-5p, miR-188-3p, miR-504-5p, miR-199a-5p, miR-93-3p, miR-328-5p, miR-483-3p and the like are more preferable.

Among BM1, from the viewpoint of higher sensitivity at the time of determination, miR-509-5p, miR-208a-5p, miR-345-3p, miR-30c-2-3p, miR-199a-5p, miR-483-3p, miR-204-3p, miR-188-3p, miR-328-5p, miR-504-5p, miR-224-3p and the like are preferable, and miR-509-5p, miR-208a-5p, miR-345-3p, miR-30c-2-3p, miR-199a-5p and the like are more preferable.

Among BM1, from the viewpoint of higher specificity at the time of determination, miR-140-3p, miR-144-5p, miR-148a-5p, miR-202-5p, miR-20b-3p, miR-539-5p, miR-99a-

5p, miR-181b-2-3p, miR-29a-3p, miR-29b-2-5p, miR-301a-5p, miR-376b-5p, miR-146a-3p, miR-216a-5p, miR-363-5p, miR-367-5p, miR-504-5p, miR-122-5p, miR-196a-5p, miR-335-3p, miR-1251-5p, miR-125b-2-3p, miR-93-3p, miR-143-3p, miR-188-3p, miR-541-3p, miR-124-3p, miR-338-5p, miR-374b-5p, miR-296-3p, miR-411-3p, miR-26a-1-3p, and the like are preferable, and miR-140-3p, miR-144-5p, miR-148a-5p, miR-202-5p, miR-20b-3p, miR-539-5p, miR-99a-5p, miR-181b-2-3p, miR-29a-3p, miR-29b-2-5p, miR-301a-5p, miR-376b-5p, miR-146a-3p, miR-216a-5p, miR-363-5p, MiR-367-5p, miR-504-5p, miR-122-5p, miR-196a-5p, miR-335-3p, miR-1251-5p, miR-125b-2-3p, miR-93-3p, MiR-143-3p and the like are more preferable.

Among the target biomarkers, at least one BM2 selected from the group consisting of miR-6070, miR-450a-2-3p, miR-4638-3p, miR-20a-3p, miR-646, miR-151a-5p, miR-151b, miR-146a-5p, miR-371a-3p, miR-21-3p, miR-578, miR-4428, miR-5095, miR-193a-3p, miR-4538, miR-492, miR-4482-5p, and miR-4768-3p can be utilized as biomarker of brain tumors, preferably including gliomas and meningiomas.

Among BM2, at least one biomarker (BM2A) selected from the group consisting of miR-151a-5p, miR-151b, miR-4428, miR-4482-5p, miR-4538, miR-4638-3p, miR-4768-3p, miR-5095, and miR-6070 is a target biomarker whose amount in a brain tumor sample tends to be higher than an amount in a healthy sample.

Among BM2, at least one biomarker (BM2B) selected from the group consisting of miR-146a-5p, miR-193a-3p, miR-20a-3p, miR-21-3p, miR-371a-3p, miR-450a-2-3p, miR-492, miR-578, and miR-646 is a target biomarker whose amount in a brain tumor sample tends to be lower than an amount in a healthy sample.

Among BM2, from the viewpoint of higher diagnostic rate at the time of determination, a miR-6070, miR-450a-2-3p, miR-4638-3p, miR-20a-3p or the like are preferable.

Among BM2, from the viewpoint of higher sensitivity at the time of determination, miR-450a-2-3p, miR-4638-3p, miR-193a-3p, miR-4428, miR-578, miR-4538, miR-646, miR-5095, miR-371a-3p and the like are preferable, and miR-450a-2-3p, miR-4638-3p, miR-193a-3p, miR-4428 and the like are more preferable.

Among BM2, from the viewpoint of higher specificity at the time of determination, miR-151b, miR-6070, miR-151a-5p, miR-20a-3p, miR-21-3p, miR-4482-5p, miR-146a-5p, miR-646, miR-371a-3p, miR-4638-3p and the like are preferable, and miR-151b, miR-6070, miR-151a-5p, miR-20a-3p, miR-21-3p and the like are more preferable.

The base sequences and the like of the target biomarkers can be specified by known databases (for example, miRBase:http://www.mirbase.org/).

The number of target biomarkers in step (1) may be only one type, but may be 2 types or more, 3 types or more, 4 types or more, 5 types or more, 6 types or more, 7 types or more, 8 types or more, 9 types or more, 10 types or more, 11 types or more, 12 types or more, 13 types or more, 14 types or more, 15 types or more, 16 types or more, 17 types or more, 18 types or more, 19 types or more, 20 types or more, 21 types or more, 22 types or more, 23 types or more, 24 types or more, 25 types or more, 26 types or more, 27 types or more, 28 types or more, 29 types or more, 30 types or more, 31 types or more, 32 types or more, 33 types or 34 types or more, 35 types or more, 36 types or more, 37 types or more, 38 types or more, 39 types or more, 40 types or more, 41 types or more, 42 types or more, 43 types or more, 44 types or more, 45 types or more, 46 types or more, 47 types or more, 48 types or more, 49 types or more, 50 types or more, 51 types or more, 52 types or more, 53 types or more, 54 types or more, 55 types or more, 56 types or more, 57 types or more, 58 types or more, 59 types or more, 60 types or more, 61 types or more, or 62 types. By combining more target biomarkers, the examination of brain tumors and the like can be performed more accurately.

In one preferred embodiment, 2 types or more, 3 types or more, 4 types or more, 5 types or more, 6 types or more, 7 types or more, 8 types or more, 9 types or more, 10 types or more, 11 types or more, 12 types or more, 13 types or more, 14 types or more, 15 types or more, 16 types or more, 17 types or more, 18 types or more, 19 types or more, 20 types or more, 21 types or more, 22 types or more, 23 types or more, 24 types or more, 25 types or more, 26 types or more, 27 types or more, 28 types or more, 29 types or more, 30 types or more, 31 types or more, 32 types or more, 33 types or more, 34 types or more, 35 types or more, 36 types or more, 37 types or more, 38 types or more, 39 types or more, 40 types or more, 41 types or more, 42 types or more, 43 types or more, or 44 types of BM1, and/or 2 types or more, 3 types or more, 4 types or more, 5 types or more, 6 types or more, 7 types or more, 8 types or more, 9 types or more, 10 types or more, 11 types or more, 12 types or more, 13 types or more, 14 types or more, 15 types or more, 16 types or more, 17 types or more, or 18 types of BM2 can be used as target biomarker.

Detection is usually performed by measuring the amount or concentration of the target biomarker. The term "concentration" is not limited to an absolute concentration, and may be a relative concentration, a weight per unit volume, a raw data measured to know an absolute concentration, or the like.

The method of detecting target biomarkers is not particularly limited as long as it is a method capable of specifically detecting part or all of the target biomarkers. Specific examples of the detecting method include RNA-seq analysis methods, RT-PCR methods, nucleic acid chip analysis methods, Northern blot method, and the like.

Specifically, when RNA-seq analysis method is used, cDNA may be prepared from RNA derived from a subject according to a conventional method, sequence analysis may be performed using a next-generation sequencer or the like, and mapping, gene expression analysis, expression level analysis or the like may be performed on the basis of the obtained data to obtain expression level data.

When a RT-PCR method is used, specifically, cDNA may be prepared from RNA derived from a subject according to a conventional method, a pair of primers (a positive strand binding to cDNA (−strand) and a reverse strand binding to the +strand) may be hybridized so that the target region can be amplified using the RNA as a template, and PCR may be performed according to a conventional method to detect the obtained amplified double-stranded DNA, for example. Note that detection of the amplified double-stranded DNA can be performed using methods of detecting labeled double-stranded DNA produced by performing the above PCR using a primer previously labeled with RI or a fluorescent substance, methods of transferring the produced double-stranded DNA to a nylon membrane or the like according to conventional methods and hybridizing it with the labeled probe to detect it, and the like.

When a nucleic acid chip analysis is used, a nucleic acid chip to which nucleic acid probes (single stranded or double stranded) are attached may be prepared, and the nucleic acid chip may be hybridized with RNA derived from a subject or nucleic acids prepared by a conventional method from the RNA, to detect the formed double strand.

When Northern blot method is used, specifically, probes may be labeled with a radioisotope (32P, 33P, or the like: RI), a fluorescent material, or the like, the probe may be hybridized with mRNA derived from the above expression system transferred to a nylon membrane or the like according to a conventional method, and then the double strand of the formed diagnostic agent and mRNA derived from the sample of the subject may be detected or measured by a radiodetector or a fluorescent detector or the like of a signal derived from the labeled substance of the probe (labeled substance such as RI or a fluorescent substance), for example.

According to the testing method of the present invention including step (1), an amount and/or a concentration of a target biomarker which is a detection indicator of a brain tumor can be provided, thereby assisting the detection of brain tumor and the like.

The test result obtained by the testing method of the present invention including step (1) can be used for the evaluation of the therapeutic effect, the elucidation of the disease state of the brain tumor, the prognosis prediction of the brain tumor, the patient stratification, the selection of the treatment method (individualized medical treatment, the treatment responsiveness), and the like.

1-2. Step (2)

The testing method of the present invention, in one aspect, further includes (2) the step of determining whether or not the subject has a brain tumor, based on the amount or concentration of the biomarker detected in step (1). According to the testing method of the present invention including step 2, it becomes possible to determine a brain tumor.

If the detected biomarker includes BM1A and/or BM2A, step (2) preferably includes (2a) step of determining that the subject has a brain tumor when the quantity or concentration of BM1A and/or BM2A detected in step (1) is above a cut-off value.

If the detected biomarker includes BM1B and/or BM2B, step (2) preferably includes (2b) step of determining that the subject has a brain tumor when the amount or concentration of BM1B and/or BM2B detected in step (1) is equal to or less than a cut-off value.

If the detected biomarker includes BM1A and/or BM2A and BM1B and/or BM2B, step (2) preferably includes (2c) step of determining that the subject has a brain tumor when the amount or concentration of BM1A and/or BM2A detected in step (1) is greater than or equal to a cut-off value and the amount or concentration of BM1B and/or BM2B detected in step (1) is equal to or less than a cut-off value.

The cut-off value can be appropriately set by a person skilled in the art in view of sensitivity, specificity, positive predictive value, negative predictive value, and the like, and can be, for example, a value determined each time or a predetermined value, based on the amount and/or concentration of a target biomarker in a body fluid collected from a subject not having brain tumor. The cut-off value may be, for example, 0.7 to 1.5 times the amount and/or concentration of the target biomarker (mean, median, or the like, for multiple subjects) in a body fluid taken from a subject not having brain tumor.

In step (2), the determination may be made by a method using a discriminant. The discriminant can be created using any discriminant analysis method capable of creating discriminants that distinguish malignant brain tumors from healthy brain tumors, including for example, but not as limiting examples, Fisher's discriminant analysis, Mahalanobis distance-based nonlinear discriminant analysis, neural networks, and Support Vector Machine (SVM), and the like.

In addition, in step (2), the determination may be performed using, for example, a neural network, a k-neighborhood method, a decision tree, a logistic regression analysis, or the like.

In a preferred embodiment of step (2), when the subject is a subject being treated for brain tumor, the cut-off value may be set to a value based on, for example, the amount and/or concentration of the target biomarker in a past sample for the same analyte, and thereby a therapeutic effect can be determined.

2. Diagnosis of Brain Tumors with Higher Accuracy

When it is determined by the testing method of the present invention including step (2) that the subject has a brain tumor, a step of applying the diagnosis by the physician of the brain tumor can be further combined to the testing method of the present invention, to diagnose brain tumor with higher accuracy. Further, since the testing method of the present invention can detect brain tumor more accurately, the method above can be combined to the testing method of the present invention, to diagnose more efficiently and more accurately as "having brain tumor".

3. Treatment of Brain Tumors

When the testing method of the present invention including step (2) determines that the subject has a brain tumor, in addition to the testing method of the present invention, or when the test method of the present invention is diagnosed as having a brain tumor as described in "2. Diagnosis of a brain tumor with higher accuracy", in addition to the combination of the testing method of the present invention and the step of applying diagnosis by a physician, (3) a treatment of the disease can be performed on the subject judged or diagnosed as having a brain tumor, thereby making it possible to treat the disease of the subject. Further, since the testing method of the present invention can detect brain tumor more accurately, step 3 can be combined to the test method of the present invention or to the combination of the testing method of the present invention and the step of applying diagnosis by a physician, to treat subjects having brain tumor more efficiently and more reliably.

Methods of treating brain tumors are not particularly limited, and include, for example, drug therapy, surgical therapy, radiation therapy, and the like. The therapeutic method may be used in combination of 1 or 2 or more. Pharmaceuticals used for the drug therapy are not particularly limited, and include, for example, biological preparations (biopharmaceuticals), non-steroidal anti-inflammatory drugs, steroids (adrenocortical steroids), and the like. The medicine may be used in combination of 1, 2, or 3 or more.

4. Brain Tumor Test Agent

The present invention relates, in one aspect thereof, to a test agent for brain tumor (sometimes referred to as a "test agent of the present invention" in this specification), including a detection agent for target biomarkers (sometimes referred to as "test agent of the present invention"). This will be described below.

The target biomarkers, brain tumors, and the like are defined in the same manner as in "1. Testing Method of Brain Tumors" above.

The detection agent of the present invention is not particularly limited as long as it can specifically detect a target biomarker. Examples of the detection agent include primers for target biomarkers, probes, and the like.

The detection agent of the present invention may be modified so long as its function is not significantly impaired.

The modifications include, for example, addition of labels, for example fluorescent dyes, enzymes, proteins, radioisotopes, chemiluminescent substances, biotin, and the like.

The fluorescent dye used in the present invention, which generally can label nucleotides and be used for detecting or quantifying nucleic acids may be preferable used, which include, for example, are not limited to, HEX (4,7,2', 4', 5', 7'-hexachloro-6-carboxylfluorescein, green fluorescent dye), fluorescein (fluorescein), NED (product name, manufactured by Applied Biosystems Co., Ltd., yellow fluorescent dye), or 6-FAM (product name, manufactured by Applied Biosystems Co., Ltd., yellow green fluorescent dye), rhodamine or a derivative thereof [for example, tetramethylrhodamine (TMR)]. Methods for labeling nucleotides with fluorescent dyes may employ suitable of the known labeling methods [see Nature Biotechnology, 14, 303-308 (1996)]. Also, commercially available fluorescent labeling kits may be used (for example, oligonucleotide ECL 3'-oligolabeling system manufactured by Amasham Pharmacia Co., Ltd., etc.).

The detection agent of the present invention can also be used by being immobilized on any solid phase. For this reason, the test agent of the present invention can be provided in the form of a substrate on which the detection agent is immobilized (for example, a microarray chip in which probes are immobilized, or the like).

The solid phase used for immobilization is not particularly limited as long as it can immobilize polynucleotides and the like, and examples thereof include glass plates, nylon membranes, microbeads, silicon chips, capillaries, and other substrates. The immobilization of the detection agent to the solid phase is not particularly limited. Immobilization methods are well known in the art depending on the type of immobilized probe, such as, for example, using a commercially available spotter (such as manufactured by Amersham Co., Ltd.) if it is a microarray [for example, in situ synthesis of oligonucleotides by photolithographic technique (Affymetrix Co., Ltd.), ink jet technique (Rosetta lnpharmatics Co., Ltd.)] and the like.

The primers, the probes, and the like are not particularly limited as long as they selectively (specifically) recognize the target biomarkers, the nucleic acid derived therefrom, and the like. Here, "selectively (specifically) recognizing" means, for example, in the Northern blot method, that target biomarkers can be specifically detected, and in the RT-PCR method, that target biomarkers or nucleic acids derived therefrom (such as cDNA) are specifically amplified, but is not limited thereto, and it is sufficient if a person skilled in the art can judge that the detected or amplified product is derived from the target biomarker.

Specific examples of the primers and probes include at least one selected from the group consisting of the polynucleotides described in (a) below and the polynucleotides described in (b) below:

(a) polynucleotides having at least 15 consecutive bases in the base sequence of the target biomarker and/or the polynucleotide complementary to the polynucleotide; and (b) polynucleotides having at least 15 bases that hybridize under stringent conditions to the base sequence of the target biomarker or the base sequence complementary thereto.

The complementary polynucleotide or complementary base sequence (complementary strand, reverse strand) means a polynucleotide or base sequence that is in a base-complementary relationship, such as A:T and G:C, to the full-length sequence of the polynucleotide consisting of the base sequence of the target biomarker, or to a partial subsequence thereof having at least 15 consecutive base sequence in the base sequence (also referred to herein for convenience as the "normal strand"). However, such a complementary strand is not limited to the case where the complete complementary sequence is formed with the base sequence of the target positive strand, and may have a complementary relationship such that it can hybridize with the target positive strand under stringent conditions. Here, the stringent conditions can be determined based on the melting temperature (Tm) of the nucleic acid binding the complex or probe, as taught in Berger and Kimmel (1987, Guide to Molecular Cloning Techniques Methods in Enzymology, Vol. 152, Academic Press, San Diego CA). For example, a washing condition after hybridization may be a condition of usually about "1×SSC, 0.1% SDS, 37° C." It is preferred that the complementary strand maintains a hybridized state with the positive strand of interest even when washed under such conditions. Although not particularly limited, it may be a washing condition of about "0.5×SSC, 0.1% SDS, 42° C." as a more stringent hybridization condition, and a washing condition of about "0.1×SSC, 0.1% SDS, 65° C." as a more stringent hybridization condition. Specifically, examples of such complementary strands include a strand consisting of a base sequence completely complementary to the base sequence of the subject positive strand, and a strand consisting of a base sequence having an identity of at least 90%, preferably 95%, more preferably 98% or more, and even more preferably 99% or more to the strand.

The primers, the probes, and the like can be designed, for example, based on the base sequence of the target biomarker, using various design programs. Specifically, a candidate sequence of the primer or probe, or a sequence comprising at least a portion of the sequence, obtained by subjecting the base sequence of the target biomarker to a design program can be used as primer or probe.

The base length of the primer, the probe, or the like is not particularly limited as long as it has a length of at least 15 consecutive bases as described above, and can be appropriately set according to the application. The base length, for example when used as a primer, may be, for example, 15 bases to 35 bases, and when used as a probe may be, for example, 15 bases to 35 bases.

The test agent of the present invention may include detection agents other than detection agents of the present invention (for example, probes for detecting nucleic acids such as other miRNA, antibodies, and the like). In this case, the test agent of the present invention may be a test agent capable of testing other diseases and conditions in addition to brain tumors. In this case, the detection agent of the present invention is included as a detection agent for brain tumor tests From this viewpoint, the test agent of the present invention is, in one aspect, a test agent for brain tumor, which contains a detection agent for brain tumor tests, consisting of the detection agent of the present invention.

The test agent of the present invention may be in the form of a composition. The composition may contain other components if necessary. The other components include, for example, bases, carriers, solvents, dispersants, emulsifiers, buffers, stabilizers, excipients, binders, disintegrants, lubricants, thickeners, humectants, colorants, perfumes, chelating agents, and the like.

The test agent of the present invention may be in the form of a kit. The kit may include, in addition to the above-described detection agent or combination containing the same, those which can be used for detecting a target biomarker in a body fluid of a subject. Specific examples of such include various reagents (for example, buffers, and the like), instruments (for example, purification, separation instruments of body fluids), and the like.

5. Method for Screening Active Ingredients of Prevention or Therapeutic Agents of Brain Tumor The present invention, in one aspect, relates to a method for screening active ingredients of prevention or therapeutic agent for brain tumor, using an amount or concentration of a target biomarker in a sample derived from a body fluid collected from an animal treated with a test substance (sometimes referred to herein as an "active ingredient screening method of the present invention"). This will be described below.

Measurements of body fluid-derived samples, target biomarkers, brain tumors, amounts or concentrations of target biomarkers, and the like are the same as the definitions in "1. Testing Method of Brain Tumors" above.

The species of the animal are not particularly limited. The species of the animal include, for example, various mammalian species such as humans, monkeys, mice, rats, dogs, cats, rabbits, and the like. Preferably, brain tumor model animals can be used.

A wide variety of test substances can be used, whether naturally existing chemicals or artificially made chemicals. In addition, not only purified compounds but also compositions obtained by mixing a variety of compounds or extracts from animals and plants can be used. The compounds are not limited to low molecular weight compounds, and also include polymer compounds such as proteins, nucleic acids, or polysaccharide.

The active ingredient screening method of the present invention more specifically includes the step of selecting the test substance as an active ingredient of a prevention or therapeutic agent for brain tumors (or a candidate substance for an active ingredient of a prevention or therapeutic agent for brain tumors) when the biomarker as indicator is BM1A and/or BM2A, and when the value of the above indicator is lower than the amount or concentration (control value) of the corresponding biomarker in a body fluid collected from an animal not treated with the test substance.

The active ingredient screening method of the present invention, as another specific example, includes the step of selecting the test substance as an active ingredient of a prevention or therapeutic agent for brain tumors (or a candidate substance for an active ingredient of a prevention or therapeutic agent for brain tumors) when the biomarker as indicator is BM1B and/or BM2B, and when the value of the above indicator is higher than the amount or concentration (control value) of the corresponding biomarker in a body fluid collected from an animal not treated with the test substance.

The corresponding biomarker means the same miRNA as the target biomarker used as indicator.

"High" means, for example, that the value of the indicator is 2, 5, 10, 20, 50, or 100 times the control value.

"Low" means, for example, that the value of the indicator is 1/2, 1/5, 1/10, 1/20, 1/50, or 1/100 of the control value.

6. Method for Assessing Inducibility or Exacerbation of Brain Tumors

The present invention, in one aspect, relates to a method for assessing the inducibility or exacerbation of brain tumor, using an amount or concentration of a target biomarker in a sample derived from a body fluid collected from an animal treated with a test substance (sometimes referred to herein as "toxicity assessment method of the present invention"). This will be described below.

Measurements of body fluid-derived samples, target biomarkers, brain tumors, amounts or concentrations of target biomarkers, species of animal, test substance and the like are the same as the definitions in "1. Testing Method of Brain Tumors" and "5. Method for Screening Active Ingredients of Prevention or Therapeutic Agents of Brain Tumor" above.

The toxicity assessment method of the present invention more specifically includes the step of determining that the test substance has inducibility or exacerbation of brain tumors when the biomarker as indicator is BM1A and/or BM2A, and when the value of the above indicator is higher than the amount or concentration (control value) of the corresponding biomarker in a body fluid collected from an animal not treated with the test substance.

The toxicity assessment method of the present invention includes, as another specific example, the step of determining that the test substance has inducibility or exacerbation of brain tumors when the biomarker as indicator is BM1B and/or BM2B, and when the value of the above indicator is lower than the amount or concentration (control value) of the corresponding biomarker in a body fluid collected from an animal not treated with the test substance.

The corresponding biomarker means the same miRNA as the target biomarker used as indicator.

"High" means, for example, that the value of the indicator is 2, 5, 10, 20, 50, or 100 times the control value.

"Low" means, for example, that the value of the indicator is 1/2, 1/5, 1/10, 1/20, 1/50, or 1/100 of the control value.

EXAMPLES

Hereinafter, the present invention will be described in detail based on Examples, but the present invention is not limited to these Examples.

Experimental Example 1. Search for Brain Tumor Biomarkers and Determination of Brain Tumor 1 miRNA were extracted from 62 urine samples of glioma patients and 100 urine samples of healthy subjects. miRNA extractions were performed using previously developed nanoscale rods (nanowires). This method is described in WO 2015/137427. It has been confirmed that this method captures urinary extracellular endoplasmic reticulum more efficiently than the conventional methods. Microarray analysis (miRNA Oligo chip, 3D-Gene (registered trademark) manufactured by Toray Corporation) was performed to select human miRNA (hsa-miR) with expression levels equal to or greater than 1.5-fold and statistically significant differences (p-values less than 0.05 by Wilcoxon rank sum test) in glioma patients compared with healthy subjects.

Target mRNA are recognized by miRNA mainly by base pairing between only 7-8 bases at the 5' end, called seed sequence, and complementary sequences in the 3' untranslated regions of the target mRNA. This seed sequence is conserved among species that differ in some miRNA, so that miRNA in which the seed sequence is conserved is thought to have a similar function across species. Therefore, microarray analysis (miRNA Oligo chip, 3D-Gene (registered trademark) manufactured by Toray Corporation) was performed to select mouse miRNA (mmu-miR) with expression levels equal to or greater than 1.5-fold in brain tumor model mice compared with healthy mice. Among the originally selected hsa-miR, 44 types of hsa-miR exhibiting expression behavior similar to that of mmu-miR were observed in hsa-miR which have been confirmed to have conservation in humans and mice. The 44 types of hsa-miR were used to determine glioma. The targets of the determination were 62 urine samples from the above-mentioned glioma patients and 100 urine samples from healthy subjects.

The 44 types of hsa-miR used for the determination are described below. hsa-miR-122-5p, hsa-miR-124-3p, hsa-miR-1251-5p, hsa-miR-125b-2-3p, hsa-miR-140-3p, hsa-miR-143-3p, hsa-miR-144-5p, hsa-miR-146a-3p, hsa-miR-148a-5p, hsa-miR-181b-2-3p, hsa-miR-188-3p, hsa-miR-196a-5p, hsa-miR-199a-5p, hsa-miR-202-5p, hsa-miR-204-3p, hsa-miR-208a-5p, hsa-miR-20b-3p, hsa-miR-216a-5p, hsa-miR-224-3p, hsa-miR-26a-1-3p, hsa-miR-27b-3p, hsa-miR-296-3p, hsa-miR-29a-3p, hsa-miR-29b-2-5p, hsa-miR-301a-5p, hsa-miR-30c-2-3p, hsa-miR-32-3p, hsa-miR-328-5p, hsa-miR-335-3p, hsa-miR-338-5p, hsa-miR-345-3p, hsa-miR-363-5p, hsa-miR-367-5p, hsa-miR-374b-5p, hsa-miR-376b-5p, hsa-miR-411-3p, hsa-miR-483-3p, hsa-miR-504-5p, hsa-miR-509-5p, hsa-miR-539-5p, hsa-miR-541-3p, hsa-miR-598-5p, hsa-miR-93-3p, hsa-miR-99a-5p.

Of these, hsa-miR-122-5p, hsa-miR-124-3p, hsa-miR-1251-5p, hsa-miR-125b-2-3p, hsa-miR-140-3p, hsa-miR-143-3p, hsa-miR-144-5p, hsa-miR-146a-3p, hsa-miR-148a-5p, hsa-miR-181b-2-3p, hsa-miR-188-3p, hsa-miR-196a-5p, hsa-miR-202-5p, hsa-miR-204-3p, hsa-miR-20b-3p, hsa-miR-216a-5p, hsa-miR-224-3p, hsa-miR-26a-1-3p, hsa-miR-27b-3p, hsa-miR-296-3p, hsa-miR-29a-3p, hsa-miR-29b-2-5p, hsa-miR-301a-5p, hsa-miR-32-3p, hsa-miR-335-3p, hsa-miR-338-5p, hsa-miR-363-5p, hsa-miR-367-5p, hsa-miR-374b-5p, hsa-miR-376b-5p, hsa-miR-411-3p, hsa-miR-504-5p, hsa-miR-539-5p, hsa-miR-541-3p, hsa-miR-598-5p, hsa-miR-93-3p, and hsa-miR-99a-5p showed higher expression levels (mean expression levels) in the glioma patients than the expression levels (mean expression levels) in the healthy subjects.

On the other hand, hsa-miR-199a-5p, hsa-miR-208a-5p, hsa-miR-30c-2-3p, hsa-miR-328-5p, hsa-miR-345-3p, hsa-miR-483-3p, and hsa-miR-509-5p showed lower expression levels (mean expression levels) in the glioma patients than the expression levels (mean expression levels) in the healthy subjects.

These miRNA, alone or in combination, were subjected to logistic regression analysis to generate determination equations for the presence or absence of glioma. The data were normalized by global normalization method, and the normalized data were used as they were. The sensitivity, specificity, and AUC for determining glioma using the generated determination equations are shown in Table 1. The cut-off values were set by Youden index.

TABLE 1

| Type of miRNA | AUC | Sensitivity (%) | Specificity (%) |
|---|---|---|---|
| hsa-miR-122-5p | 0.595 | 23 | 97 |
| hsa-miR-124-3p | 0.570 | 21 | 93 |
| hsa-miR-1251-5p | 0.666 | 39 | 96 |
| hsa-miR-125b-2-3p | 0.619 | 29 | 96 |
| hsa-miR-140-3p | 0.597 | 19 | 100 |
| hsa-miR-143-3p | 0.637 | 34 | 95 |
| hsa-miR-144-5p | 0.573 | 15 | 100 |
| hsa-miR-146a-3p | 0.545 | 11 | 98 |
| hsa-miR-148a-5p | 0.532 | 6 | 100 |
| hsa-miR-181b-2-3p | 0.607 | 23 | 99 |
| hsa-miR-188-3p | 0.759 | 61 | 94 |
| hsa-miR-196a-5p | 0.571 | 18 | 97 |
| hsa-miR-199a-5p | 0.715 | 71 | 67 |
| hsa-miR-202-5p | 0.629 | 26 | 100 |
| hsa-miR-204-3p | 0.680 | 68 | 65 |
| hsa-miR-208a-5p | 0.783 | 90 | 59 |

TABLE 1-continued

| Type of miRNA | AUC | Sensitivity (%) | Specificity (%) |
|---|---|---|---|
| hsa-miR-20b-3p | 0.613 | 23 | 100 |
| hsa-miR-216a-5p | 0.537 | 10 | 98 |
| hsa-miR-224-3p | 0.638 | 50 | 84 |
| hsa-miR-26a-1-3p | 0.657 | 45 | 90 |
| hsa-miR-27b-3p | 0.654 | 48 | 88 |
| hsa-miR-296-3p | 0.623 | 32 | 92 |
| hsa-miR-29a-3p | 0.559 | 13 | 99 |
| bsa-miR-29b-2-5p | 0.607 | 23 | 99 |
| hsa-miR-301a-5p | 0.599 | 21 | 99 |
| hsa-miR-30c-2-3p | 0.664 | 73 | 55 |
| hsa-miR-32-3p | 0.633 | 42 | 89 |
| hsa-miR-328-5p | 0.703 | 61 | 73 |
| hsa-miR-335-3p | 0.595 | 23 | 97 |
| hsa-miR-338-5p | 0.649 | 39 | 93 |
| hsa-miR-345-3p | 0.802 | 85 | 69 |
| hsa-miR-363-5p | 0.569 | 16 | 98 |
| hsa-miR-367-5p | 0.561 | 15 | 98 |
| hsa-miR-374b-5p | 0.587 | 26 | 93 |
| hsa-miR-376b-5p | 0.567 | 15 | 99 |
| hsa-miR-411-3p | 0.669 | 45 | 92 |
| hsa-miR-483-3p | 0.701 | 69 | 68 |
| hsa-miR-504-5p | 0.743 | 52 | 98 |
| hsa-miR-509-5p | 0.450 | 100 | 4 |
| hsa-miR-539-5p | 0.589 | 18 | 100 |
| hsa-miR-541-3p | 0.640 | 35 | 94 |
| hsa-miR-598-5p | 0.621 | 37 | 89 |
| hsa-miR-93-3p | 0.712 | 48 | 96 |
| hsa-miR-99a-5p | 0.532 | 6 | 100 |
| Combination of 44 | 0.985 | 98 | 91 |

Experimental Example 2. Search for Brain Tumor Biomarkers and Determination of Brain Tumor 2

110 urine samples of brain tumor patients (including both glioma patients and meningioma patients) and 100 urine samples of healthy subjects were analyzed, as targets, for miRNA expression in the same manner as in Experimental Example 1, and biomarkers were searched, and determination was performed. In the present experimental example, the data were normalized by global normalization method, and after the data were normalized, all values of 0 were set to 1, they were log-transformed (base 2), and the values of 3 or less were truncated to 0. In addition, in the present experimental example, miRNA were narrowed down by L1 regularization, and then a determination equation was created, and then cross validation was also performed to confirm the determination equation. The determination equation of this experimental example is shown below.

$$Pr(Y=1\mid X)=\frac{1}{1+e^{-(\alpha+\beta_1\cdot x_1+\beta_2\cdot x_2+\beta_3\cdot x_3+\dots)}} \quad \text{[Equation 1]}$$

Y: Objective variable to be predicted (scalar value). Value range 0 to 1.

To be tagged as [smaller than 0.5: negative example (healthy), 0.5 or larger: positive example (lung cancer)]

$X=[x_1, x_2, x_3, \ldots, x_{2565}]$: Explanatory variable vector

This time miRNA test data of subjects (normalized)

$[\beta_1, \beta_2, \ldots, \beta_{2565}]$: Partial regression vector. Weights of explanatory attributes This time, weight for each miRNA data item.

Estimation from past data is required.

$\alpha$: Intercept (scalar value). Estimated from the sample data at the same time as the deviation regression coefficient.

e: Napier's constant (=2.71828 . . . )

18 types of hsa-miR used for the determination are described below. hsa-miR-146a-5p, hsa-miR-151a-5p, hsa-miR-151b, hsa-miR-193a-3p, hsa-miR-20a-3p, hsa-miR-21-3p, hsa-miR-371a-3p, hsa-miR-4428, hsa-miR-4482-5p, hsa-miR-450a-2-3p, hsa-miR-4538, hsa-miR-4638-3p, hsa-miR-4768-3p, hsa-miR-492, hsa-miR-5095, hsa-miR-578, hsa-miR-6070, hsa-miR-646.

Of these, hsa-miR-151a-5p, hsa-miR-151b, hsa-miR-4428, hsa-miR-4482-5p, hsa-miR-4538, hsa-miR-4638-3p, hsa-miR-4768-3p, hsa-miR-5095 and hsa-miR-6070 showed higher expression levels (mean expression levels) in the brain tumor patients than the expression levels (mean expression levels) in the healthy subjects.

On the other hand, hsa-miR-146a-5p, hsa-miR-193a-3p, hsa-miR-20a-3p, hsa-miR-21-3p, hsa-miR-371a-3p, hsa-miR-450a-2-3p, hsa-miR-492, hsa-miR-578, and hsa-miR-646 showed lower expression levels (mean expression levels) in the brain tumor patients than the expression levels (mean expression levels) in the healthy subjects.

The sensitivity, specificity, and diagnostic rate of brain tumor determination are shown in Table 2.

TABLE 2

| Type of miRNA | Diagnostic rate | Sensitivity (%) | Specificity (%) |
|---|---|---|---|
| hsa-miR-146a-5p | 67 | 66.7 | 67.4 |
| hsa-miR-151a-5p | 67.6 | 55.5 | 81 |
| hsa-miR-151b | 67.6 | 52.7 | 84 |
| hsa-miR-193a-3p | 60.9 | 83.5 | 36 |
| hsa-miR-20a-3p | 72.6 | 69.6 | 75.8 |
| hsa-miR-21-3p | 65.9 | 62 | 70.2 |
| hsa-miR-371a-3p | 66.4 | 70.4 | 62 |
| hsa-mtR-4428 | 61.7 | 82 | 39.4 |
| hsa-miR-4482-5p | 55.2 | 42.9 | 68.8 |
| hsa-miR-450a-2-3p | 74.3 | 96.4 | 50 |
| hsa-miR-4538 | 60.6 | 78.4 | 41 |
| hsa-miR-4638-3p | 73 | 84.7 | 60.2 |
| hsa-miR-4768-3p | 52.9 | 53.8 | 51.8 |
| hsa-miR-492 | 57.3 | 63.6 | 50.4 |
| hsa-miR-5095 | 61.4 | 70.9 | 51 |
| hsa-miR-578 | 64.3 | 79.1 | 48 |
| hsa-miR-6070 | 76.1 | 69.8 | 83 |
| hsa-miR-646 | 68.8 | 72.2 | 65 |
| Combination of 18 | 96.2 | 97.8 | 94.4 |

The invention claimed is:

1. A method of testing and treating a brain tumor, the method comprising (1) measuring the amount or concentration of miR-6070 in a urine sample derived from a human subject, (2) detecting an amount or concentration of miR-6070 measured in (1) that is higher than an amount or concentration of miR-6070 in a urine sample from a subject not having a brain tumor, and determining that the subject has a brain tumor; and (3) treating the brain tumor in the subject with one or more of a drug therapy, a surgical therapy and a radiation therapy;

wherein, measuring the amount or concentration of miR-6070 in (1) comprises one or more method selected from RNA-seq analysis, RT-PCR, nucleic acid chip analysis, and northern blot.

2. The method of claim 1, wherein said urine sample comprises urinary extracellular vesicles.

3. A method of diagnosing a brain tumor in a human subject, comprising:

(a) providing a sample of urinary extracellular vesicles obtained from a human subject;

(b) detecting the level of miR-6070 in the sample from the human subject;

(c) comparing the level of miR-6070 in the sample from the human subject to a level of miR-6070 in a sample of urinary extracellular vesicles obtained from a healthy human without a brain tumor;

(d) determining that the level of miR-6070 in the sample from the human subject is higher than the level of miR-6070 the sample from the healthy human;

(e) diagnosing the human subject as having a brain tumor; and (f) treating the brain tumor in the subject with one or more of a drug therapy, a surgical therapy and a radiation therapy.

4. The method of claim 3, wherein said brain tumor is a glioma or meningioma.

5. The method of claim 1, wherein said brain tumor is a glioma or meningioma.

* * * * *